United States Patent

Farr et al.

[11] Patent Number: 5,997,571
[45] Date of Patent: Dec. 7, 1999

[54] NON-OCCLUDING PHOTOTHERAPY PROBE STABILIZERS

[75] Inventors: Norman Farr, Monument Beach; Lincoln S. Baxter, Centerville; Edward L. Sinofsky, Dennis, all of Mass.

[73] Assignee: CardioFocus, Inc., West Yarmouth, Mass.

[21] Appl. No.: 08/992,930

[22] Filed: Dec. 17, 1997

[51] Int. Cl.⁶ ................................................. A61B 17/36
[52] U.S. Cl. .................................. 607/92; 606/7; 606/15
[58] Field of Search .................... 606/15, 7, 198; 607/88, 89, 92

[56] References Cited

U.S. PATENT DOCUMENTS

| Re. 34,544 | 2/1994 | Spears . | |
|---|---|---|---|
| 4,336,809 | 6/1982 | Clark . | |
| 4,878,492 | 11/1989 | Sinosky et al. . | |
| 4,998,930 | 3/1991 | Lundahl . | |
| 5,053,033 | 10/1991 | Clarke . | |
| 5,074,871 | 12/1991 | Groshong | 606/170 |
| 5,125,925 | 6/1992 | Lundahl . | |
| 5,188,602 | 2/1993 | Nichols | 604/113 |
| 5,188,635 | 2/1993 | Radtke | 606/14 |
| 5,632,767 | 5/1997 | Sinofsky | 607/89 |
| 5,637,877 | 6/1997 | Sinofsky | 250/492.1 |
| 5,643,253 | 7/1997 | Baxter et al. | 606/17 |
| 5,649,978 | 7/1997 | Samson | 623/1 |
| 5,700,243 | 12/1997 | Narciso, Jr. | 604/102 |
| 5,824,005 | 10/1998 | Motamedi et al. | 606/15 |
| 5,855,565 | 1/1999 | Bar-Cohen et al. | 604/104 |

*Primary Examiner*—Michael Peffley
*Assistant Examiner*—Roy Gibson
*Attorney, Agent, or Firm*—Thomas J. Engellenner; Paul D. Durkee; Nutter, McClennen & Fish, LLP

[57] ABSTRACT

Phototherapeutic instruments are disclosed for providing substantially uniform energy distribution to a major portion of an area exposed during phototherapy. These instruments include an element for directing radiation toward the walls of a lumen and a device for centering the radiation directing element within the lumen. The instruments also allow the flow of blood, therapeutic fluid, or air past the exposure site. The instruments are particularly useful as part of a fiber optic-based medical laser system for photodynamic therapy within the bronchia of the lung, blood vessels or other liquid-filled lumens.

19 Claims, 4 Drawing Sheets

NON-OCCLUDING PHOTOTHERAPY PROBE STABILIZERS

BACKGROUND OF THE INVENTION

The technical field of this invention is phototherapy and, in particular, instruments employing optical fibers or other flexible light waveguides to deliver radiation to a targeted biological site.

Fiber optic phototherapy is an increasingly popular modality for the diagnosis and/or treatment of a wide variety of diseases. For example, some have proposed the use of fiber-delivered radiation to treat artherosclerotic disease. U.S. Pat. No. 4,878,492 (Sinofsky et al. '492), herein incorporated by reference, discloses the used of infrared radiation to heat blood vessel walls during balloon angioplasty in order to fuse the endothelial lining of the blood vessel and seal the surface. Another application of fiber-delivered radiation is disclosed in U.S. Pat. No. 5,053,033 (Clarke '033), herein incorporated by reference. Clarke '033 teaches that restenosis following angioplasty can be inhibited by application of UV radiation to the angioplasty site to kill smooth muscle cells which would otherwise proliferate in response to angioplasty-induced injuries to blood vessel walls.

Moreover, fiber optic delivery systems have been incorporated in endoscopic or catheter-based instruments to deliver photoactivating radiation to light sensitive drugs within a body lumen or cavity. U.S. Pat. No. 4,336,809 (Clark '809), herein incorporated by reference, and U.S. Reissue Pat. No. RE 34,544 (Spears '544), herein incorporated by reference, disclose that hematoporphyrin dyes and the like selectively accumulate in atheromatous plaque or tumorous tissue. These patents further teach that when cancerous tissue has taken up the dye, such tissue can be preferentially destroyed by radiation, typically by high intensity red light.

When a patient is catheterized with a light-emitting catheter that is inserted into the diseased artery or other body lumen, the placement is often likely to be offset from the longitudinal axis of the lumen. Such a configuration will result in a nonuniform exposure of the walls of the lumen by the light-emitting portion of the catheter. Nonuniform radiation exposure of the walls can result in damage to the lumen and/or nonuniform activation of the absorbed hematoporphyrin-like dyes.

In one embodiment of the Spears '544 patent, a light-emitting balloon catheter is employed to address the "centering problem." The catheter includes an inflatable balloon secured to the distal end of the catheter tube for inflation with gas from a remote source, and optical fibers which are disposed within the catheter, such that upon inflation of the balloon, light can be transmitted through the interior of the balloon to irradiate the target region of the lumen.

Although such a balloon catheter can act to center the light-emitting portion of the catheter, the balloon also acts to obstruct the flow of blood, therapeutic fluids, or air. Phototherapeutic treatments can take more than fifteen minutes. Thus, the duration of these procedures can preclude using a balloon catheter as a device for centering the light-emitting portion of the optical fiber since blocking a bloodstream or airway for an extended period of time is often impractical.

Accordingly, there exists a need for better apparatus for fiber-optic phototherapy. In particular, devices that can provide substantially uniform radiation exposure of a patient's lumen by centering a light-emitting catheter without occluding the lumen would meet a particularly important need in the field of minimally-invasive phototherapeutic surgery. Moreover, a device that can help stabilize the phototherapeutic instrument in operation (such as within an airway or blood vessel) would also be particularly useful. Uniform radiation exposure of the walls of the lumen while allowing flow of fluids past the light delivery device will make fiber optic phototherapy more practical and predictable.

SUMMARY OF THE INVENTION

Phototherapeutic instruments are disclosed for providing substantially uniform energy distribution to a major portion of an area exposed during phototherapy. These instruments include an element for directing radiation toward the walls of a lumen and a device for centering the radiation directing element within the lumen. The instruments also allow the flow of blood, therapeutic fluid, or air past the exposure site. The instruments are particularly useful as part of a fiber optic-based medical laser system for phototherapy. As used herein the term "optical fiber" is intended to encompass optically transmissive waveguides of various shapes and sizes.

In one embodiment, a fiber optic apparatus for use in applying phototherapeutic radiation inside a body lumen includes an optical fiber having a proximal and a distal end, a diffusive tip assembly connected to the distal end of the optical fiber, and a sheath surrounding the diffusive tip assembly. The proximal end of the optical fiber is adapted for coupling to a source of phototherapeutic radiation. The diffusive tip assembly is adapted for diffusing radiation toward the wall of the lumen. The surrounding sheath has a non-occluding projection element which is capable of projecting outward, away from the diffusive tip assembly, subsequent to insertion of the diffusive tip assembly and the surrounding sheath into the lumen such that the non-occluding projection element presses against the wall of the lumen, substantially centering the optical fiber within the lumen.

In a preferred embodiment, the sheath includes a flexible, fluted region having expansion elements which expand by flexure upon axial compression of the fluted region. The phototherapeutic apparatus includes a retractor element coupled to the distal end of the sheath for inducing axial compression. In one embodiment, the distal end of the diffusive tip assembly and the distal end of the surrounding sheath can be connected so that axial compression of the sheath can be effected at a location remote from the diffusive tip assembly, causing the fluted region to expand.

The optical fiber and the surrounding sheath can be constructed to provide sufficient clearance therebetween for delivery of therapeutic fluids to the radiation site. The fluted region can be made of radio-opaque Teflon® filler material with fillers such as barium or bismuth. The fluted region is preferably constructed to provide sufficient clearance between the surrounding sheath and the walls of the lumen and between adjacent expansion elements of the fluted region so as to allow flow of air, therapeutic fluid, or blood, past the exposure site. Furthermore, the surrounding sheath can include a plurality of fluted regions.

In an alternative embodiment, a series of projections can be activated to protrude from the catheter body and contact the lumen walls. Such projections can be rigid or inflatable. For example, a plurality of small balloons which do not occlude fluid passage can be employed as an alternative centering mechanism.

In another aspect of the invention, a diffusive tip assembly is disclosed for use with various centering devices of the present invention. The tip assembly includes a light transmissive, tubular housing alignable with, and adapted to receive, the distal end of the fiber. The tip assembly serves as a waveguide for light propagating through the fiber. Furthermore, the tubular housing can contain radiation-scattering particles and the tip assembly can include a reflective end. Thus, as radiation propagates through the diffusive tip assembly, the radiation is scattered. When radiation impinges on the side walls of the tubular housing at an angle that exceeds the critical angle for internal reflection, the radiation exits the tip. Radiation which is not emitted during this initial pass through the tip is reflected by at least one end surface or end cap and returned through the tip. During this second pass, the remaining radiation (or at least a major portion of this returning radiation) again encounters the scatterers which provide further radial diffusion of the radiation.

In yet another aspect of the invention, novel materials and structures are disclosed for diffusive tip assemblies to alleviate or reduce the potential for contact-adhesion between the tip and nearby tissue segments. This aspect of the invention is particularly useful in connection with endoscopic and/or catheter-based phototherapy to ensure that the diffusive tip does not bond accidentally to the body lumen or blood vessel wall during procedures. In one embodiment, fluoropolymer materials, such as Teflon® materials and the like, are disclosed as preferred materials for the tip enclosure and/or the outer cladding or coating to inhibit contact-adhesion between the tip assembly and biological tissue during procedures. Most preferably, the Teflon® material is a Teflon® FEP material (a polyperfluoroethylene-propylene copolymer). Other Teflon® materials such as Teflon® PFA (a polytetrafluoroethylene polymer with perfluoroalkoxy side chains) and Teflon® PTFE (polytetrafluoroethylene) also can be useful in certain applications.

The structures disclosed herein represent a substantial step forward in the delivery of therapeutic radiation to remote treatment sites. The surrounding sheath designs of the present invention permit the uniform delivery of phototherapeutic radiation to a large volume of tissue, while permitting the flow of blood, therapeutic fluid, or air past the exposure site. Furthermore, the diffusive assembly designs of the present invention permit the delivery of radiation at power levels on the order of tens of Watts or more. In fact, diffusive tip assemblies have been successfully constructed to deliver over 100 Watts of power in a diffuse pattern to a treatment site, allowing the clinician to perform therapy rapidly and uniformly to a large volume of tissue.

The invention will next be described in connection with certain preferred embodiments. However, it should be clear that various changes and modifications can be made by those skilled in the art without departing from the spirit and scope of the invention.

DETAILED DESCRIPTION

Figure 5:
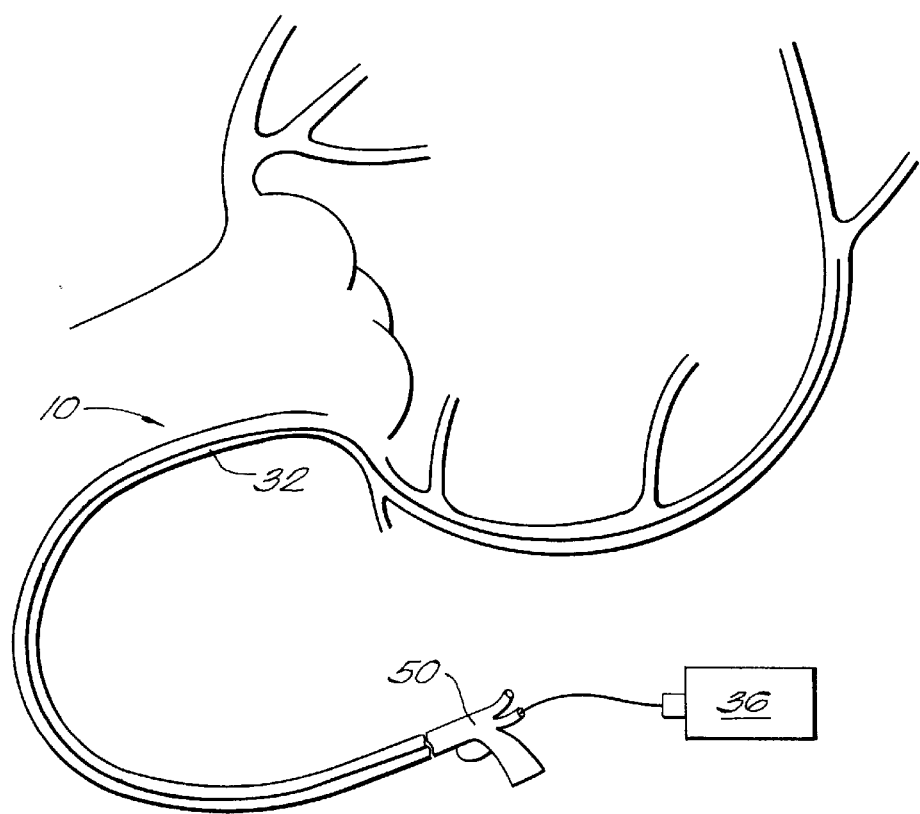
FIG. 5 is a schematic view of the phototherapeutic apparatus of FIG. 1 inserted into a patient's lumen.
Figure 4:
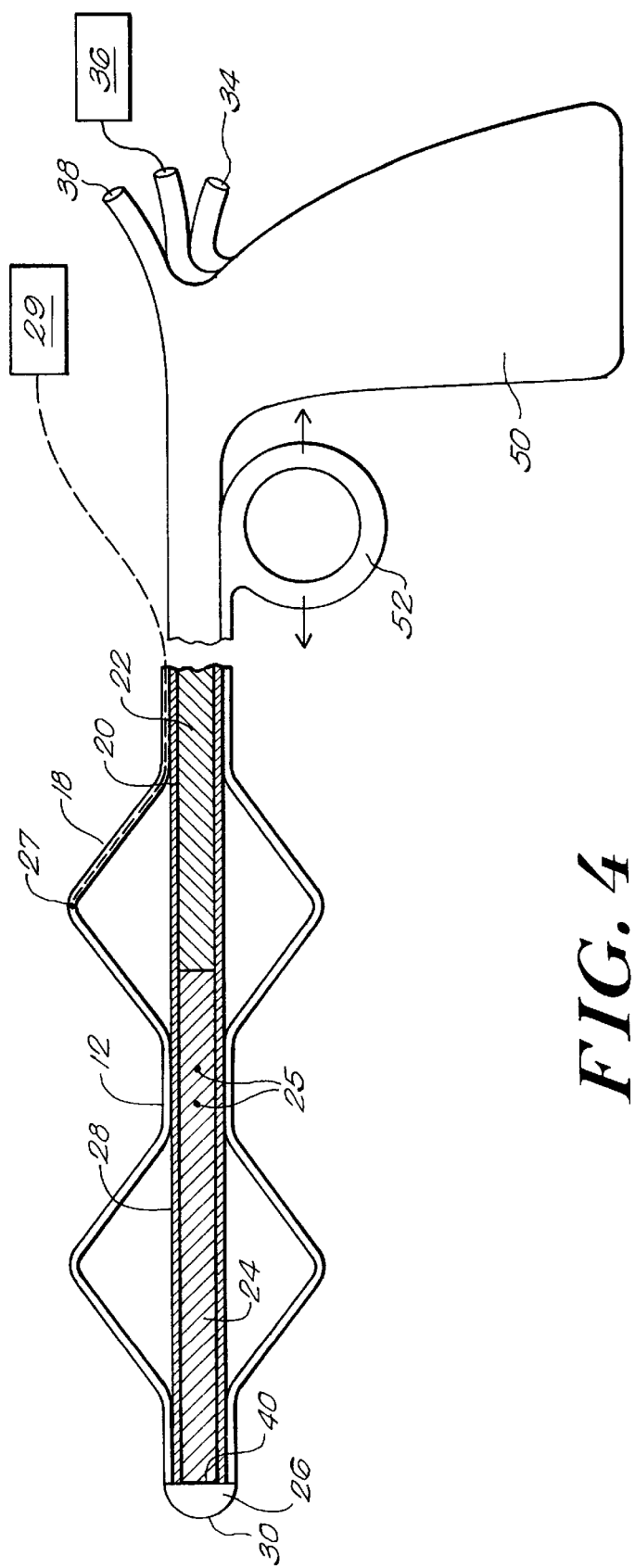
FIG. 4 is a cross-sectional illustration of the phototherapeutic apparatus of FIG. 1, along its longitudinal axis.

In FIGS. 1, 1A, 4 and 5, one embodiment of a phototherapeutic apparatus 10 according to the invention is illustrated having a tubular sheath 12 and an inner optically-transmissive fiber element 14. In FIG. 5, this phototherapeutic apparatus 10 is shown schematically in operation. The diffuser apparatus with its fluted tubular sheath is coupled to a source of phototherapeutic radiation 36, (e.g., a laser) and positioned within a patient's body to provide phototherapy. According to one embodiment, the diffuser assembly can fit within a standard guiding catheter 32. The catheter 32, as illustrated in FIG. 4, includes an operating handle 50 with a trigger element 52 connected to the fiber element 14 forming a retractor element. The catheter further includes electrical sensing elements 34 and/or at least one additional channel 38 for introduction of saline or therapeutic solutions. The proximal end of the optically-transmissive fiber element 14 is coupled to a source of phototherapeutic radiation 36.

Returning to FIG. 1, the distal end of the sheath 12 is fluted such that axial compression of the sheath results in expansion of expansion elements 18 in the fluted region 16. This expansion forces the expansion elements into the sides of a body lumen, as can be seen in FIGS. 6A–6C.

Figure 6A:
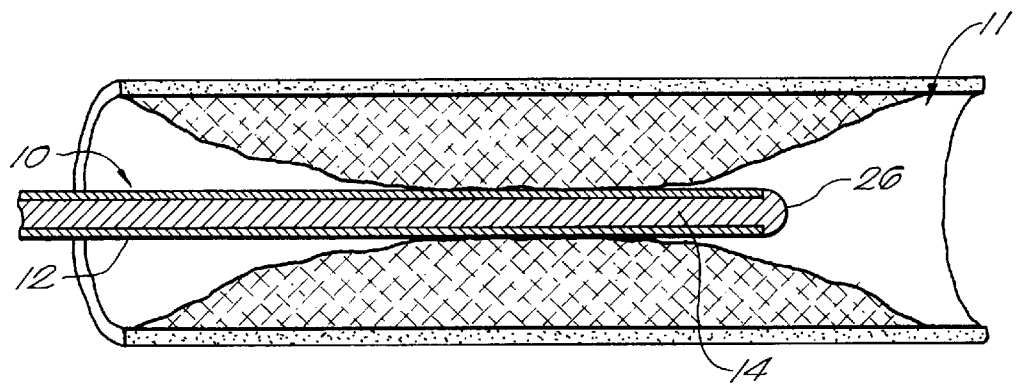
FIG. 6A illustrates the distal end of a phototherapeutic apparatus of the present invention inserted into a patient's lumen and deployed in an initial position prior to the fluted region of the sheath contacting the inner surface of the lumen.

In FIG. 6A, the use of the phototherapeutic apparatus of the present invention is shown schematically. As illustrated, the instrument 10 is positioned next to a segment of a patient's lumen where insertion and radiation is desired. As shown, the apparatus includes an outer sheath 12 having a flexible fluted region 16 and an inner optically-transmissive fiber element 14 with tip 26. In one preferred embodiment, the fiber 14 and sheath 12 are constructed with sufficient clearance to permit saline or other therapeutic liquids to be released during the procedure. In particular, saline flushing of the distal end of the optically-transmissive fiber element 14 may be desirable to cool the tissue surface proximal to the treatment site.

Figure 6B:
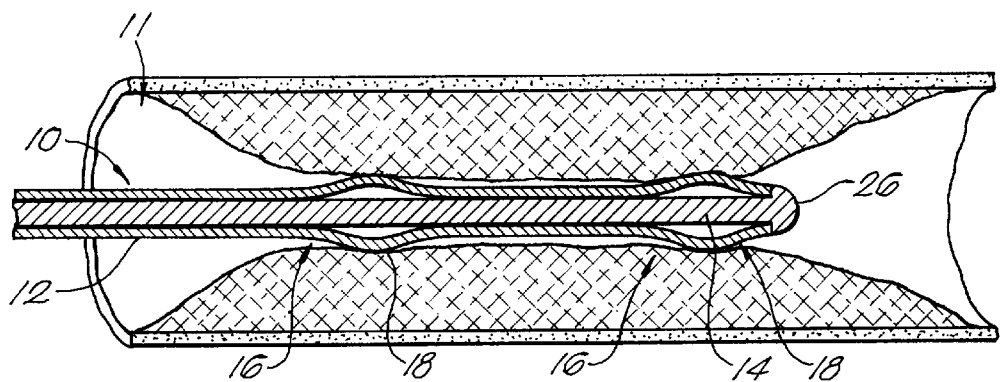
FIG. 6B is a further illustration of the apparatus of FIG. 6A after initial expansion of the fluted region of the sheath of the apparatus.

In FIG. 6B, initial expansion of the sheath 12 is shown. In this illustration, the optically-transmissive fiber is inserted into the patient's lumen. Next the fluted region 16 is expanded to center the phototherapy device 10 within the patient's lumen. The expansion of the fluted region is accomplished by axial compression of the sheath 12. In one embodiment, the axial compression of the sheath is accomplished by pulling back on the optically-transmissive fiber element 14. The fiber element 14 can be connected to the housing 28 and the end cap 26. These elements can be bonded by melting. Furthermore, the distal end of the fiber element 14 and the sheath 12 can be thermally bonded or assembled. Thus, subsequent to insertion of the phototherapeutic device, an operator can cause relative sliding motion of the fiber element 14 and the sheath 12 to axially compress the sheath 12. One method of achieving the relative sliding motion and axial compression is to pull back on the optical fiber element 14 while holding the sheath 12 still. The trigger element 52 is provided as a convenient means for pulling back on the optical fiber element 14. Thus, the trigger element 52 is coupled to the proximal end of the fiber element 14 and the proximal end of the sheath 12 so that the trigger element can control the expansion of the non-occluding expansion elements 18. An alternative method of achieving axial compression is pushing the sheath 12 forward, while holding the fiber element 14 still. The compression of the sheath 12, in turn, causes the expansion of the flexible fluted region 16, thereby centering the device within the patient's lumen.

Figure 6C:
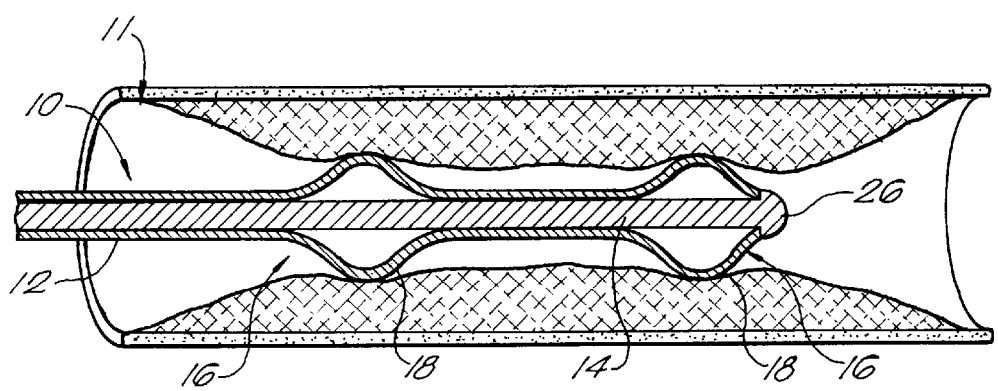
FIG. 6C further illustrates the expansion of the sheath of the phototherapeutic apparatus of FIG. 6A.

In FIG. 6C, sheath 12 has completely expanded in the patient's lumen pushing into the surrounding tissue and centering the phototherapy device 10 in the lumen. Importantly, the fluted region allows fluids, including gases, to pass the phototherapy device 10 while the device is in operation. According to the embodiment illustrated in FIG. 1, there is sufficient clearance, e.g., about 0.02 mm to about 2 mm, between the optical fiber 20 and the surrounding sheath 12 to facilitate delivery of therapeutic liquids to the radiation site. Further, to provide a preferred amount of clearance between the wall of the lumen and the distal end of the phototherapeutic apparatus, and between the expansion elements 18 of the fluted region 16, the length of the illustrated expansion elements are about 1 mm to about 5 cm, and the width of the expansion elements are about 0.2 mm to about 1 cm. This design allows reduction of hematocrit by flushing out the fluted region 16.

Figure 2:
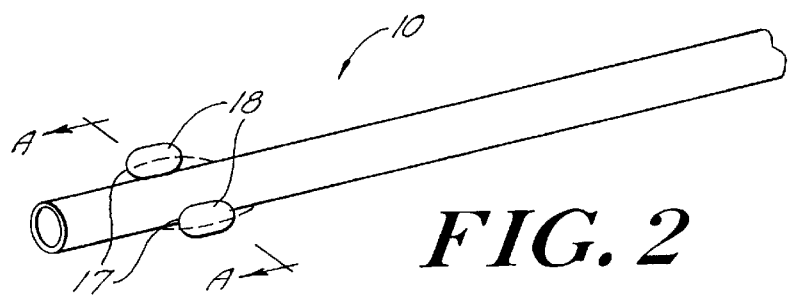
FIG. 2 is a schematic, perspective view of a second embodiment of a phototherapeutic apparatus' distal end in accordance with the present invention.
Figure 2A:
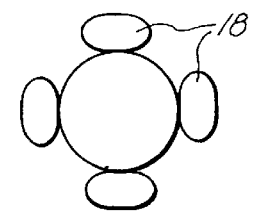
FIG. 2A is a cross-sectional view of the apparatus of FIG. 2, along line A—A.
Figure 2B:
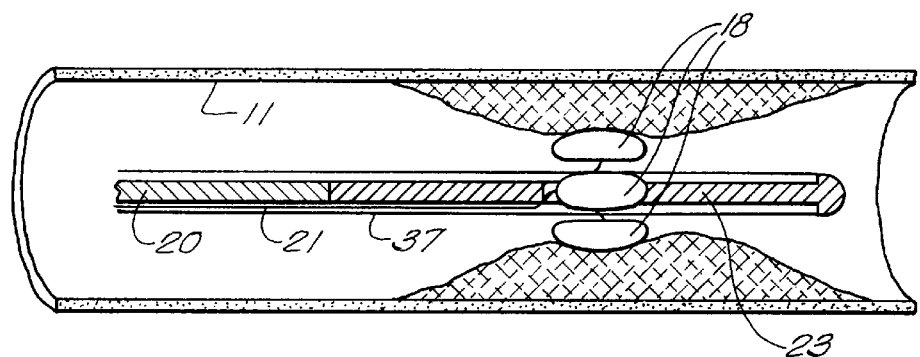
FIG. 2B is a cross-sectional illustration of the phototherapeutic apparatus of FIG. 2, along its longitudinal axis.

With reference to FIGS. 2, 2A, and 2B, another embodiment of a phototherapeutic apparatus includes distinct balloon expansion elements 18. In the representation of FIG. 2B, the wall of the main artery undergoing treatment is represented by the numeral 11. For treatment, an operator inserts the light-emitting portion of the catheter into the diseased blood vessel to a position adjacent the deposit of atheromatous plaque to be lysed. The catheter includes a tube 37 and balloon expansion elements 18 attached to the outside of the distal end of the tube 37. The tube contains an optical fiber 20 and a gas delivery conduit 21. The deflated state of the balloon elements is indicated by the dotted lines 17 in FIG. 2.

Inflation of the balloon expansion elements is provided for by the gas delivery conduit 21 which is in fluid communication with the interior of the balloon elements and which can be connected, at its opposite end, to a source of pressurized gas. Importantly, upon inflation the balloon expansion elements do not occlude flow of air or liquid past the phototherapy treatment site. At least one optical fiber 20 is provided for transmitting light from an external source to a light-emitting tip 23. The balloon expansion elements are preferably composed of material that transmits the light emitted by the light-emitting tip 23.

Figure 3:
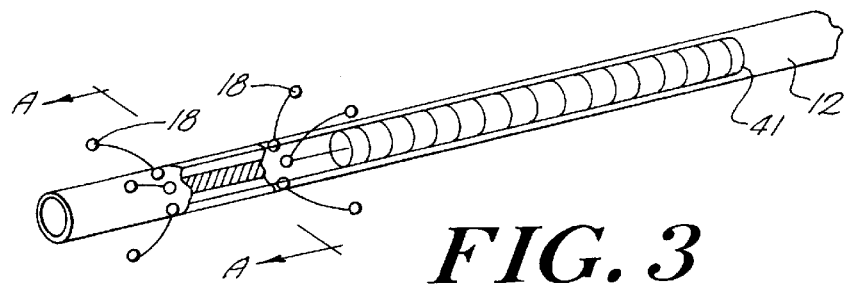
FIG. 3 is a schematic, perspective view of a third embodiment of a phototherapeutic apparatus' distal end in accordance with the present invention.
Figure 1A:
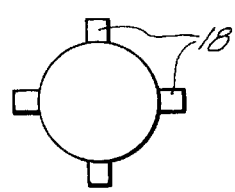
FIG. 1A is a cross-sectional view of the apparatus of FIG. 1, along line A—A.
Figure 3A:
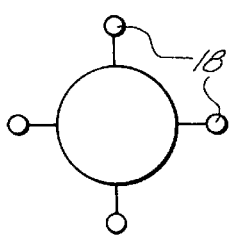
FIG. 3A is a cross-sectional view of the apparatus of FIG. 3, along line A—A.

Yet another embodiment of a phototherapeutic apparatus according to the invention is shown in FIGS. 3 and 3A. Rigid expansion elements 18 are extended once the apparatus is inserted in a body lumen for treatment of the lumen. The rigid expansion elements are extended by distal movement of the expansion actuating element 41 relative to the tubular sheath 12. Again the rigid expansion elements 18 do not occlude flow of air or liquid past the phototherapy treatment site.

Figure 1:
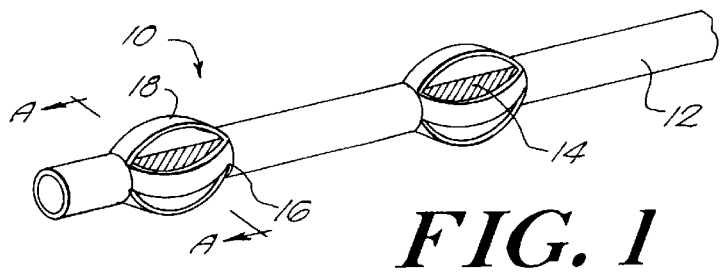
FIG. 1 is a schematic, perspective view of the distal end of a phototherapeutic apparatus in accordance with the present invention.

FIG. 4 is a more detailed cross-sectional view of the distal end of the apparatus of FIG. 1. The optically-transmissive element is shown having an optical fiber 20 with an optically transmissive core 22 surrounded by a cladding, and buffer coating. The end face of fiber core 22 is inserted into a housing 28 which contains a scattering medium 24 with optional individual scatterer particles 25. Preferably, the medium 24 has a greater refractive index than the housing 28. At the distal end of the optical fiber 20, an end cap 26 can be disposed. Optionally, the end cap may also be fitted with a reflective mirror 40. The end cap can further be ground or polished to an atraumatic blunt or rounded end 30. At least one dosimetry detector 27 is included in an expansion element 18. The dosimetry detector is connected to a control element 29 and is preferably located at the longitudinal midpoint of the expansion element 18.

Light propagating through the optical fiber core 22 is transmitted into the scatterer medium and scattered in a cylindrical pattern along the length of the assembly 14. Each time the light encounters a scatterer particle, it is deflected and, at some point, the net deflection exceeds the critical angle for internal reflection at the interface between the housing 28 and the medium 24. When this happens the light will exit. The housing can either be made sufficiently long to ensure that virtually all of the light entering it is eventually scattered and diffused in a single path, or as noted above, a reflective mirror can be fitted to the distal end of each diffuser assembly. When a mirror is employed, light propagating through the medium 24 will be at least partially scattered before it reaches mirror 40. Light which does not exit during this initial pass through the tip will be reflected by mirror 40 and returned through the tip assembly. During the second pass, the remaining radiation (or at least a major portion of this returning radiation) again encounters the scatterers which provide further circumferential diffusion of the light. The dosimetry detector 27 and control element 29 detect the amount of radiation delivered to the exposure area of the lumen. The control element 29 can automatically terminate the transmission of phototherapeutic radiation once the amount of radiation delivered reaches a predetermined level or the control element 29 can merely display the amount of radiation delivered to the exposure area.

An exemplary manufacturing process suitable for joining a diffuser assembly to a glass-clad or polymer-clad optical fiber having an outer diameter of about 50 to about 1000 micrometers includes stripping off the buffer from the end of the optical fiber, e.g., exposing about two or three millimeters of the inner fiber core and its cladding. (It is not necessary to strip the cladding away from the core.) Prior to stripping, the fiber end face preferably should be prepared and polished as known in the art to minimize boundary or interface losses. A transparent tubular structure which will form the housing for the scatterer medium is then slipped over the prepared fiber end and, preferably slid beyond the fiber end. For example, if a tip assembly of about 20 millimeters is desired, the tubing can be about 100 millimeters long and slid over about 75 millimeters of the fiber, leaving an empty lumen of about 25 millimeters in front of the fiber end face. In one preferred embodiment, the housing is Teflon® FEP (tetrafluoroethylene) tubing, available, for example, from Zeus Industries (Raritan, N.J.).

The assembly is then injected with a scatterer-loaded material, such as a silicone, epoxy or other polymeric material(if a solid diffuser is desired) or a suitable liquid, such as water or a deuterium oxide solution, containing colloidal scatterer particles, such as silica, alumina, or titania, (if a liquid diffuser is desired). One exemplary scatterer medium can be formulated by mixing 70 parts of clear silicone, Mastersil™ Formula 151-Clear (available from Masterbond, Inc. of Hackensack, N.J.) with one part of titania filled silicone, Mastersil™ Formula 151-White (also available from Masterbond), and a conventional silicone curing or hardening agent. The tube lumen should be completely filled with the silicone, epoxy or other carrier mixture to avoid entrapment of air bubbles. The reflector (e.g., an aluminum, gold or other reflector-coated plug) is inserted into the distal end of the tube. The reflector at the distal end of the scatterer tube can be a deposited metal or dielectric coating. In one preferred embodiment, a room temperature hardening agent is used and the diffuser assembly is simply allowed to solidify overnight.

It should be clear that the manufacturing processes described above are merely illustrative, and various alternative techniques can be practiced to construct the fiber tip assemblies of the present invention. For example, automated extrusion methods and/or injection molding approaches can be employed to mass produce fibers with integral diffusive tip assemblies.

Various other diffusive tip assemblies can be employed in the present invention. For a detailed discussion of various alternative embodiments see commonly-owned co-pending U.S. patent application Ser. No. 08/827,631, filed Apr. 10, 1997, entitled "PHOTOTHERAPY METHODS AND APPARATUS", by Edward L. Sinofsky, incorporated herein by reference.

Various materials can be used to form the outer sheath 12 including, for example, Teflon® and other fluorocarbon polymers. In one embodiment, the fluted region is made of white fluoropolymers to further homogenize angular output of the radiation. The fluted region can also be made radio-paque with barium or bismuth fillers. The struts can be formed by axial slices at various locations on the sheath. For example to construct a four strut fluted region, one would make four longitudinal cuts into the sheath, separated by 90° from each other. The length of the cuts will determine the radial extent of the fluted region. In one embodiment it may also be desirable to fill the sheath polymer with a radio-opaque substance, such as barium in order to permit visualization under angiography.

It will thus be seen that the invention efficiently attains the objects set forth above, among those made apparent from the preceding description. Since certain changes can be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of scope of the invention which, as a matter of language, might be said to fall therebetween.

Having described the invention, what is claimed as new and desired to be secured by Letters Patent is:

1. A fiber optic apparatus for use in applying phototherapeutic radiation inside a body lumen, said apparatus comprising an optical fiber having a proximal end and a distal end, the proximal end adapted for coupling to a source of phototherapeutic radiation and the distal end adapted for directing such radiation into biological tissue;

the apparatus further comprising a sheath including proximal and distal ends and a longitudinal axis, the sheath surrounding the distal end of the optical fiber and having a first non-occluding expansion element spaced apart from a second non-occluding expansion element, the first and second expansion elements being capable of projecting outward, away from the optical fiber, subsequent to insertion of the distal end of the optical fiber and the surrounding sheath into the lumen, such that the non-occluding first and second expansion elements contact the wall of the lumen, substantially centering the optical fiber within the lumen.

2. The apparatus of claim 1, wherein the sheath further comprises a flexible, fluted region in which the first and second expansion elements are located, wherein the expansion elements expand by flexure upon axial compression of the fluted region.

3. The apparatus of claim 2 wherein the clearance between the optical fiber and the surrounding sheath is about 0.02 mm to about 2 mm so as to facilitate delivery of therapeutic liquids to the radiation site.

4. The apparatus of claim 2 wherein the fluted region is made of a radio-opaque material.

5. The apparatus of claim 4 wherein the radio-opaque material comprises a tetrafluoroethylene material with a radio-opaque filler, and wherein the filler is formed from a radiopaque filler selected from the group consisting of barium and bismuth.

6. The apparatus of claim 2 wherein the apparatus further includes a trigger element coupled to the proximal end of the optical fiber for controlling expansion of the non-occluding expansion elements.

7. The apparatus of claim 2 wherein the fluted region comprises white fluorocarbon polymers.

8. The apparatus of claim 2 wherein the lengths of the expansion elements are about 1 mm to about 5 cm and the widths of the expansion elements are about 0.2 mm to about 2 cm so as to provide sufficient clearance between the lumen and the surrounding sheath and between the expansion elements of the fluted region, facilitating flow of gas and liquid past the radiated biological tissue.

9. The apparatus of claim 1, wherein the fiber optic apparatus further comprises a diffusive tip assembly having a proximal end connected to the distal end of the optical fiber, the diffusive tip assembly being adapted for diffusing radiation toward the wall of the lumen.

10. The apparatus of claim 9 wherein the diffusive tip assembly further comprises a light transmissive housing adapted for coupling with the distal end of the optical fiber, the housing having a light scattering medium disposed therein.

11. The apparatus of claim 10 wherein the housing further includes an end cap having a reflective surface such that light radiation propagating through said fiber enters the scattering medium and a portion of the radiation is emitted outward through said housing, and another portion is reflected by the reflective surface of the end cap for re-transmission through said scattering medium and further outward emission.

12. The apparatus of claim 10 wherein the housing is made of a polymeric material.

13. The apparatus of claim 12 wherein the polymeric material of the housing is a fluorocarbon polymer.

14. The apparatus of claim 10 wherein the scattering medium further comprises a medium having light-scattering particles dispersed therein, and wherein the scattering particles are chosen from the group consisting of alumina, silica, titania compound and mixtures thereof.

15. The apparatus of claim 2 wherein the optical fiber distal end is thermally bonded to the sheath such that proximal movement of the optical fiber relative to sheath causes axial compression of the sheath.

16. The apparatus of claim 9 wherein the diffusive tip assembly comprises an atraumatic blunt distal end.

17. A fiber optic apparatus for use in applying phototherapeutic radiation inside a body lumen, said apparatus comprising:
   an optical fiber having a proximal end and a distal end, the proximal end adapted for coupling to a source of phototherapeutic radiation and the distal end adapted for directing such radiation into biological tissue;
   a sheath having proximal and distal ends and a longitudinal axis, the sheath surrounding the distal end of the optical fiber and including a flexible, fluted region having non-occluding expansion elements which are capable of projecting outward, away from the optical fiber, subsequent to insertion of the distal end of the optical fiber and the surrounding sheath into the lumen, such that the expansion elements contact the wall of the lumen, substantially centering the optical fiber within the lumen, the expansion elements further comprising a dosimetry detector; and
   a retractor means coupled to the distal end of the sheath for inducing axial compression.

18. The apparatus of claim 17 wherein the dosimetry detector is located in the middle of the length of the expanding element such that when the expansion element expands by flexure upon axial compression of the fluted region, the dosimetry detector is located in selected proximity to the wall of the lumen.

19. A fiber optic apparatus for use in applying phototherapeutic radiation inside a body lumen, said apparatus comprising
   an optical fiber having a proximal end and a distal end, the proximal end adapted for coupling to a source of phototherapeutic radiation;
   a diffusive tip assembly having a proximal end connected to the distal end of the optical fiber, the diffusive tip assembly being adapted for diffusing radiation toward the wall of the lumen;
   the apparatus further comprising a sheath surrounding the diffusive tip assembly and having a first non-occluding expansion element spaced apart from a second non-occluding expansion element, the first and second expansion elements being capable of projecting outward, away from the diffusive tip assembly, subsequent to insertion of the diffusive tip assembly and the surrounding sheath into the lumen, such that the expansion elements contact the wall of the lumen, substantially centering the optical fiber within the lumen.

* * * * *